(12) United States Patent
Braman et al.

(10) Patent No.: US 8,686,129 B2
(45) Date of Patent: Apr. 1, 2014

(54) METHODS FOR THE SEPARATION OF BIOLOGICAL MOLECULES USING SULFOLANE

(75) Inventors: Jeffrey C. Braman, Carlsbad, CA (US); Lee S. Basehore, Lakeside, CA (US); Natalia Novoradovskaya, San Diego, CA (US)

(73) Assignee: Agilent Technologies, Inc., Loveland, CO (US)

( * ) Notice: Subject to any disclaimer, the term of this patent is extended or adjusted under 35 U.S.C. 154(b) by 868 days.

(21) Appl. No.: 11/688,652

(22) Filed: Mar. 20, 2007

(65) Prior Publication Data
US 2008/0234474 A1 Sep. 25, 2008

(51) Int. Cl.
*C07H 21/00* (2006.01)

(52) U.S. Cl.
USPC ............... 536/25.4; 536/25.41; 536/25.42

(58) Field of Classification Search
None
See application file for complete search history.

(56) References Cited

U.S. PATENT DOCUMENTS

| | | | | |
|---|---|---|---|---|
| 3,164,004 | A * | 1/1965 | King, Jr. .................. 73/24.06 |
| 4,900,677 | A | 2/1990 | Hewitt |
| 5,637,687 | A | 6/1997 | Wiggins |
| 5,990,301 | A * | 11/1999 | Colpan et al. ............. 536/25.4 |
| 6,020,186 | A | 2/2000 | Henco et al. |
| 6,178,034 | B1 * | 1/2001 | Allemand et al. ........... 359/265 |
| 6,180,778 | B1 * | 1/2001 | Bastian et al. ............. 536/25.4 |
| 6,297,371 | B1 * | 10/2001 | Colpan et al. ............. 536/25.3 |
| 6,407,178 | B1 * | 6/2002 | Kolbe et al. ............... 525/328.2 |
| 6,815,541 | B1 | 11/2004 | Usui et al. |
| 6,946,250 | B2 * | 9/2005 | Bastian et al. ............. 435/6.14 |
| 6,958,392 | B2 | 10/2005 | Fomovskaia et al. |
| 7,074,916 | B2 * | 7/2006 | Bastian et al. ............. 536/25.4 |
| 7,235,362 | B2 * | 6/2007 | Braman et al. ............. 435/6.14 |
| 7,238,478 | B2 * | 7/2007 | Braman et al. ............. 435/6.14 |
| 7,326,577 | B2 * | 2/2008 | Shults et al. ............... 436/176 |
| 2005/0009045 | A1 | 1/2005 | Greenfield et al. |
| 2005/0026159 | A1 * | 2/2005 | Robbins et al. ............. 435/6 |
| 2006/0099605 | A1 * | 5/2006 | Hall et al. ................ 435/6 |
| 2009/0239768 | A1 * | 9/2009 | Hansen et al. .............. 506/16 |

FOREIGN PATENT DOCUMENTS

| | | | |
|---|---|---|---|
| GB | 1117677 | * | 6/1968 |
| JP | 2005151975 A | | 6/2005 |
| WO | WO 2007-149791 | | 12/2007 |

OTHER PUBLICATIONS (R) Burwell et al. "Solvent Characteristics of Tetramethylene Sulfone [Sulfolane]," J. American Chemical Society, 81(14), 3799-4000 (Jul. 20, 1959).*
PCT International Search Report and Written Opinion received in Application No. PCT/US2008/056125, mailed Jul. 28, 2008, pp. 1-12.
Absolutely RNA nanoprep Kit. Instruction Manual, Revision A, Agilent Technologies, Inc., 2008.
R. Formosa et al.: DNA-based Fish Species Identification Protocol, J. Vis. Exp. Apr. 28, 2010, (38), pii: 1871, doi: 10.3791/187, Abstract; see also: http://www.jove.com/details.php?id=1871 (complete article).
Castagnolo et al., "Ionic enthalpies of transfer frm water to water-sulfolane mixtures," Journal of Solution Chemistry (1979): 8(7):501-508.

* cited by examiner

*Primary Examiner* — Lawrence E Crane

(57) ABSTRACT

The present invention provides a method for the isolation of biological molecules by the adsorption of the molecules onto a mineral substrate in the presence of an appropriate mixture of salts and sufolane. Preferably, the biological molecules are nucleic acids. Compositions and kits for performing the process according to the invention are also provided.

22 Claims, 9 Drawing Sheets

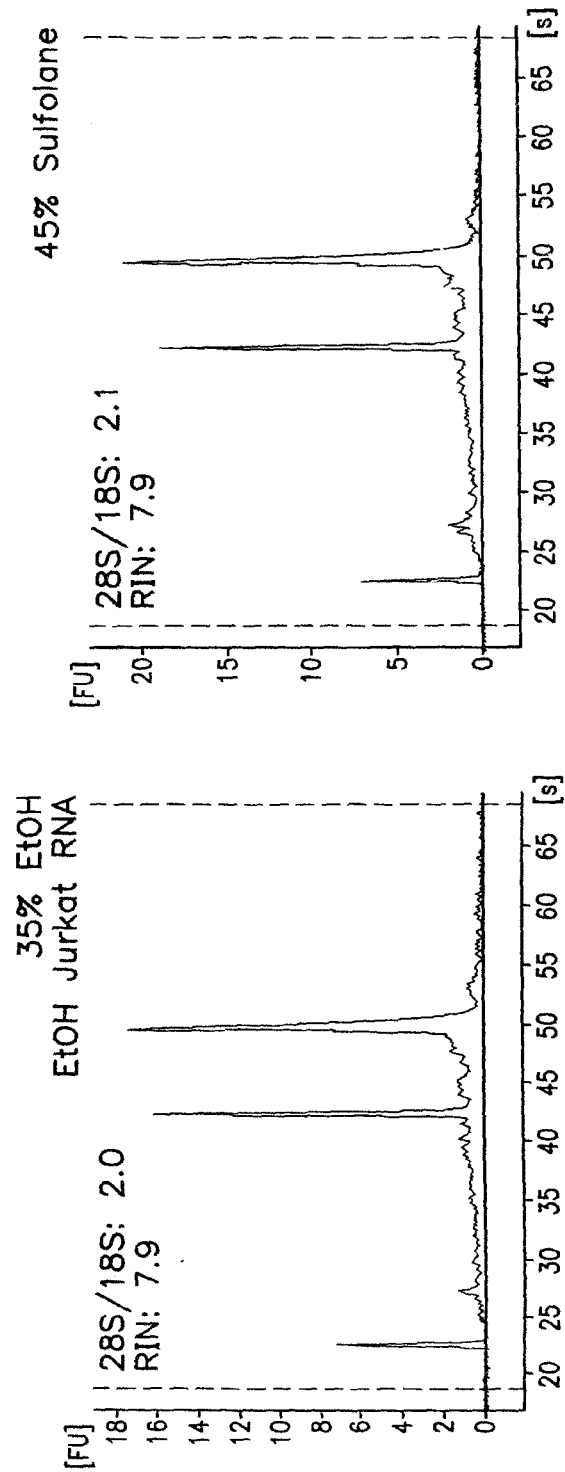

| | |
|---|---|
| RNA Area: | 8.1 |
| RNA Concentration: | 10  ng/μl |
| rRNA Ratio [28s / 18s]: | 1.2 |
| RNA Integrity Number [RIN]: | 8.9  [B.02.02] |

```
SEQUENCE LISTING

<160> NUMBER OF SEQ ID NOS: 3

<210> SEQ ID NO 1
<211> LENGTH: 21
<212> TYPE: DNA
<213> ORGANISM: Homo sapiens

<400> SEQUENCE: 1
tgcacgtgga tcctgagaac t                                             21

<210> SEQ ID NO 2
<211> LENGTH: 22
<212> TYPE: DNA
<213> ORGANISM: Homo sapiens

<400> SEQUENCE: 2
aattctttgc caaagtgatg gg                                            22

<210> SEQ ID NO 3
<211> LENGTH: 22
<212> TYPE: DNA
<213> ORGANISM: Homo sapiens

<400> SEQUENCE: 3
cagcacgttg cccaggagcc tg                                            22
```

METHODS FOR THE SEPARATION OF BIOLOGICAL MOLECULES USING SULFOLANE

BACKGROUND OF THE INVENTION

1. Field of the Invention

The present invention relates to the field of isolation and purification of biological molecules. More specifically, the present invention pertains to methods, compositions, and kits for separating and purifying nucleic acids.

2. Description of Related Art

Sulfolane is a clear, colorless liquid commonly used in the chemical industry as an extractive distillation solvent or reaction solvent (see FIG. 1). It was originally developed as a solvent to purify butadiene (see, for example, U.S. Pat. No. 4,090,923). Sulfolane has several applications in molecular biology. It has been used along with other liquids to form an upper and lower phase in a method to extract nucleic acids (see, for example, U.S. Pat. No. 6,815,541). It has also been employed to improve cell lysis and solubilization in a process for rapid isolation of high molecular weight DNA (see, for example, U.S. Pat. No. 4,900,677). Furthermore, it can be used as an aprotic solvent to deactivate ribonucleases and denature proteins in general (see, for example, U.S. Pat. No. 5,637,687). In addition, it has been reported that it can also be used to enhance PCR (see, for example, U.S. Pat. No. 6,949,368).

Isolation of biological molecules, such as DNA and RNA, and their subsequent analysis is a fundamental part of molecular biology. Analysis of nucleic acids is crucial to gene expression studies, not just in basic research, but also in the medical field of diagnostic use. For example, diagnostic tools include those for detecting nucleic acid sequences from minute amounts of cells, tissues, and/or biopsy materials, and for detecting viral nucleic acids in blood or plasma. The yield and quality of the nucleic acids isolated and purified from a sample has a critical effect on the success of any subsequent analyses.

Isolation of nucleic acids from a biological sample usually involves lysing the biological sample by, for example, mechanical action and/or chemical action followed by purification of the nucleic acids. Previously, purification of nucleic acids was performed using methods such as cesium chloride density gradient centrifugation (which is time-consuming and expensive) or extraction with phenol (which is considered unhealthy for the user). In a typical final step, ethanol precipitation was used to concentrate the nucleic acids, which resulted in lower yields of the isolated nucleic acids.

Many of the methods currently used to isolate nucleic acids are based on the adsorption of the nucleic acid on glass or silica particles in the presence of a chaotropic salt (see, for example, Vogelstein, B. and Gillespie, D., "Preparative and analytical purification of DNA from agarose", *Proc. Natl. Acad. Sci. USA* 76:615-619, 1979; U.S. Pat. Nos. 5,234,809; and 6,180,778).

However, methods that allow easy isolation of nucleic acids, proteins, and other molecules from various cells and tissues, that have improved yields, that provide better quality of isolated product, and that do not require organic solvent extraction or ethanol precipitation are still needed in the art.

SUMMARY OF THE INVENTION

The present invention addresses needs in the art by providing methods, compositions, and kits for purifying biological molecules from samples, such as cell lysates and tissue lysates. The invention is based, at least in part, on the discovery that biological molecules, such as nucleic acids, can bind to a mineral substrate in the presence of sulfolane. More specifically, it has been found that single-stranded nucleic acid molecules can bind to a mineral substrate in the presence of chaotropic salts and sulfolane. For example, the invention encompasses the use of a mixture of at least one chaotropic salt, detergent-lysed cells (e.g., mammalian cells, such as those from blood and those cultured in flasks), and glass fiber filters to capture genomic DNA on the glass fiber filter, while allowing RNA to pass through. Addition of sulfolane to the flow-through mixture allows RNA to bind to glass substrates, such as glass fiber. Among other things, this discovery can be used to preferentially separate single-stranded nucleic acids from double-stranded nucleic acids. The method of this invention eliminates organic solvent extractions and ethanol precipitations. Biological molecules purified or isolated using the method of the present invention, such as nucleic acids isolated by the method, can have high yields and can be of high quality. Indeed, in embodiments, the purified or isolated materials are used directly for subsequent analyses.

In a first aspect, the invention provides a method of isolating biological molecules. In a preferred embodiment, the method can be used to isolate double-stranded and/or single-stranded nucleic acids. In general, the method comprises contacting a sample comprising a biological molecule, such as a single-stranded nucleic acid, a double-stranded nucleic acid, or both, with sulfolane in the presence of a chaotropic salt to form a composition, and exposing the composition to at least one mineral substrate for a sufficient amount of time for the biological molecule to become adsorbed to the mineral substrate. In preferred embodiments, the sample comprises predominantly single-stranded nucleic acid, and it predominantly is adsorbed to the mineral substrate. Viewed from another perspective, the method can comprise treating the sample with at least one mineral substrate, wherein the treatment conditions are adjusted with an appropriate mixture of salts, especially chaotropic substances, and sulfolane, such that the biological molecule (e.g., single-stranded nucleic acid) fraction is adsorbed on the mineral substrate. Preferably, the mixture is an aqueous mixture. The concentration of sulfolane can be adjusted to preferentially bind one or more biological molecules. For example, in the presence of one or more chaotropic salts and in the absence of sulfolane, DNA can preferentially bind to the mineral support as compared to RNA. Addition of sulfolane to the mixture containing unbound RNA and chaotropic salt(s) allows for binding of the RNA to a second mineral support. In the method, one or more optional washing steps can be performed at times selected by those practicing the invention. Further, where the method is used for isolation of DNA, RNase may be added at any point to remove contaminating RNA molecules. The adsorbed material of interest can be released from the mineral support by elution in an appropriate liquid, such as water or an aqueous buffer, such as one having a low ionic strength. Where the single stranded nucleic acid of interest is RNA, the method can comprise exposing the composition to at least one mineral support in the presence of one or more chaotropic salts and sulfolane thereby allowing the RNA to bind to the mineral support. The mineral support and adsorbed nucleic acids can be exposed to DNase to remove from the mineral substrate any contaminating DNA that might have been adsorbed. According to the method, single-stranded nucleic acid adsorbed on the mineral substrate can be eluted under conditions of low ionic strength or simply with water.

In another aspect, the invention provides compositions that can be used to isolate one or more biological molecules, such as a nucleic acid. The composition may comprise sulfolane and one or more salts. For example, the composition may comprise sulfolane at a concentration of 10-80% and a chaotropic salt at a concentration of 1-8 Molar (M). The composition may, in embodiments, comprise a buffer to help maintain a desired pH or pH range. Thus, the buffer may comprise sulfolane and one or more salts in a lysis buffer. The compositions preferably comprise one or more biological molecules, such as nucleic acids, proteins, carbohydrates, and/or others.

In an additional aspect, the invention provides kits comprising one or more containers that independently contain sulfolane, a mineral support, one or more cell lysis solutions, wash solutions, elution solutions, or two or more of these in combination. The kits can be used, for example, to isolate biological molecules, such as nucleic acids. In general, the kits comprise materials, reagents, supplies, etc. for use in practicing a method of the present invention. Thus, in various embodiments, the kit may comprise sulfolane, one or more buffers such as cell lysis buffers, DNase, DNase reconstitution buffer, DNase digestion buffer, RNase, RNase reconstitution buffer, RNase digestion buffer, high salt wash buffer, low salt wash buffer, and/or elution buffer. The kit may likewise comprise columns, such as prefiltration columns to filter the sample, columns to adsorb nucleic acid molecules, and/or columns to purify proteins.

BRIEF DESCRIPTION OF THE DRAWINGS

The accompanying drawings, which constitute a part of this specification, illustrate several embodiments of the invention and, together with the written description, serve to explain various principles of the invention. It is to be understood that the drawings are not to be construed as a limitation on the scope or content of the invention.

DETAILED DESCRIPTION OF VARIOUS EMBODIMENTS OF THE INVENTION

Figure 1:
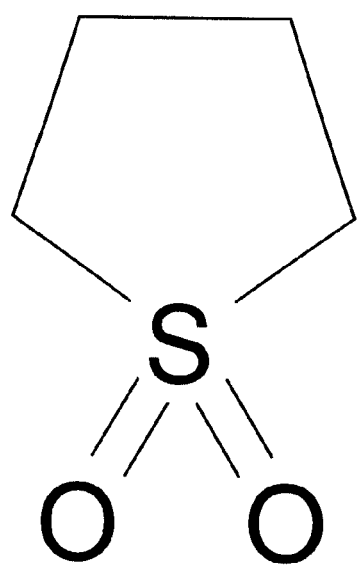
FIG. 1 depicts the structure of sulfolane.

Reference will now be made in detail to various exemplary embodiments of the invention. The following description is provided to give details on certain embodiments of the invention, and should not be understood as a limitation on the full scope of the invention.

Broadly speaking, the present invention provides methods, compositions, and kits for separating, purifying, and/or isolating biological molecules from a sample in the presence of an appropriate mixture of salts and sulfolane. Accordingly, in one aspect, the invention provides a method of isolating biological molecules, such as nucleic acids and proteins, in the presence of sulfolane. In general, the method comprises exposing one or more biological molecules to sulfolane and a mineral support for a sufficient amount of time for some or all of the biological molecules to be adsorbed or otherwise bound to the mineral support. The biological molecule of interest may be one bound to the mineral support, or one found in the un-bound fraction. For example, in a composition comprising a nucleic acid and a protein, the nucleic acid may be bound to the mineral support under the described conditions, whereas the protein may remain unbound. In this way, both molecules may be purified away from each other. Subsequently, salts, buffers, solvents, etc. can be added to the optimal conditions for purification of a variety of protein species employing filters, resins, etc. The method may also comprise exposing the biological molecule to one or more salts, such as chaotropic salts. The method may also comprise removing the sulfolane, salts, and/or any unbound substances, by washing the mineral support and bound material, and/or releasing the bound material from the mineral support.

In a preferred embodiment, the invention provides a method of isolating or purifying nucleic acids, including single-stranded and double-stranded nucleic acids using sulfolane. The method comprises exposing a sample comprising the nucleic acids to be isolated or purified to at least one mineral substrate (also referred to herein as a mineral support or solid support), wherein the exposing conditions comprise an appropriate mixture of salts, especially chaotropic substances, and sulfolane, such that the nucleic acids are adsorbed on the mineral substrate. Preferably, the mixture is an aqueous mixture. Optionally, the adsorbed sample on the substrate is washed with buffer after adsorption. In addition, in methods for isolating or purifying RNA, DNA molecules that are also adsorbed to the substrate can be removed by exposing the mineral support and bound material to DNase (preferably RNase-free) under suitable conditions and for an adequate amount of time for digestion of the DNA to occur. Conversely, in methods for isolating or purifying DNA, RNA molecules that are also adsorbed to the substrate can be removed by exposing the mineral support and bound material to RNase (preferably DNase-free) under suitable conditions and for an adequate amount of time for digestion of the RNA to occur.

The present invention can also be utilized to selectively bind either a single-stranded or double-stranded nucleic acid to a mineral substrate. Nucleic acid binding to the mineral substrate is a function of the amount of sulfolane and salts present during binding, among other factors. Under certain conditions of salt, and where sulfolane concentrations are high (for example, at concentrations of 50% or more sulfolane), both types of nucleic acid (DNA and RNA) bind to the mineral support. Under other conditions, where the sulfolane and/or salt concentrations becomes less than a defined value, one or neither of the nucleic acids will bind to the mineral support to any substantial extent. However, in between these two conditions, RNA and DNA will bind to the mineral support to a different extent and thus, the concentrations of salts and sulfolane can be adjusted to selectively bind predominantly one nucleic acid. This method, therefore, is a way to separate nucleic acids by differential binding of DNA and RNA in the presence of sulfolane and salts. In one embodiment, RNA is selectively bound to the mineral substrate under conditions of lower concentrations of sulfolane (e.g., 20%-40% sulfolane by volume) and the DNA molecules predominantly flow through. Additional sulfolane can be added to the flow-through fraction containing predominantly DNA from the first mineral substrate, thereby allowing the DNA to bind to a second mineral support. For example, the sulfolane concentration can be raised to 45% or more to effect DNA binding. Other variations can be envisioned and utilized to take advantage of the differential binding of the nucleic acids to a mineral substrate in the presence of sulfolane and salts.

Figure 2:
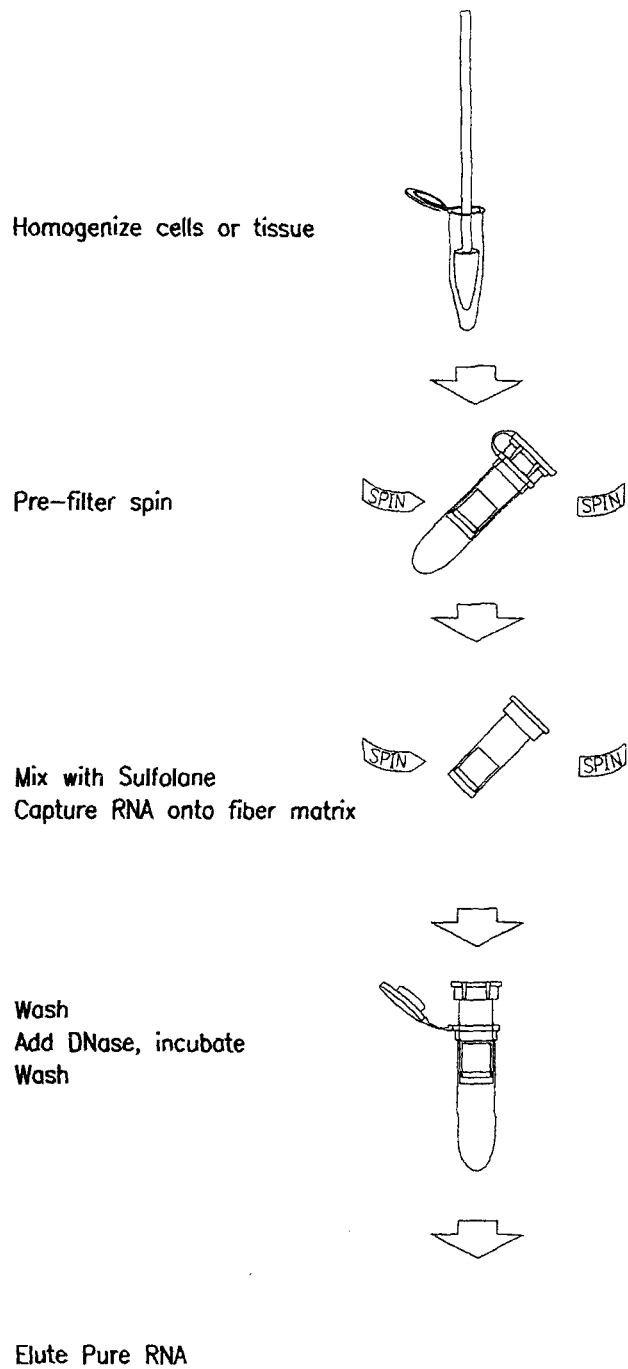
FIG. 2 depicts a schematic picture of an embodiment of a method of nucleic acid purification according to the invention.

As an example of the present invention, this method may be incorporated into a miniprep kit to perform a method to isolate RNA molecules (see, for example, FIG. 2). In this method, the cells or tissue are homogenized in a buffer to lyse the cells. The lysate is added to a prefilter column and spun to capture large DNA molecules. The filtrate comprising RNA molecules and a high salt concentration is mixed with sulfolane and added to a spin column comprised of a silica-based fiber matrix. The RNA bound to the spin column matrix is optionally washed with at least one low salt wash and/or high salt wash. An optional DNase treatment can also be performed on the spin column bound with RNA molecules. Following an optional second washing regimen as described above, the RNA is eluted with a low ionic strength buffer or water.

In an embodiment, the method comprises filtering of the sample prior to binding of the RNA to the mineral support in the presence of sulfolane. For example, a sample comprising a mixture of nucleic acids can be pre-filtered by passing the sample over one or more filters so that large, predominantly double-stranded DNA is captured by the prefilter. The flow through fraction, which comprises predominantly RNA, can then be adsorbed to a mineral substrate in the presence of an appropriate aqueous mixture of salts and sulfolane. After optionally performing washing steps and an optional DNase digestion to remove any residual DNA from the mineral substrate, elution of the RNA adsorbed on the mineral substrate can be accomplished with a solution, preferably an aqueous solution, having low ionic strength. According to this method, the large molecules, which can include genomic DNA, other cellular macromolecules, and/or extracellular debris such as connective tissue etc., are captured by the prefilter as a result of their relatively large size. Thus, in the method, the molecules captured by the prefilter can be released at a desired time by chemical and/or physical means. One simple and gentle way to remove the captured material is to flow a liquid across the prefilter in the opposite direction from the original filtration. Doing so will dislodge a substantial portion of the entrapped material, which is then substantially purified from smaller material (for example, DNA is now purified from contaminating RNA). The macromolecules separated from the prefilter then can be directly analyzed or can be further purified by a variety of methods, including but not limited to being adsorbed to a mineral substrate in the presence of an appropriate mixture of sulfolane and an optimal concentration of salt or salts.

Depending on the sample constitution, after prefiltration, the flow-through fraction may comprise predominantly smaller double-stranded nucleic acids, such as small DNA molecules. These molecules can then be adsorbed to a mineral substrate in the presence of an appropriate aqueous mixture of salts and sulfolane. After optionally performed washing steps and an optional RNase step to remove contaminating RNA from the mineral substrate, the smaller DNA molecules can be eluted from the mineral substrate with an aqueous solution having low ionic strength that may or may not be heated. In general, the small DNA molecules that are found in the flow-through fraction are about 6 kb or less, such as from about 6 kb to about 4 kb, or from about 4 kb to about 1 nucleotide. In preferred embodiments, the DNA molecules are about 1 kb or less.

In another embodiment, the method of the invention comprises the isolation of a specific protein from a biological sample. In this case, salts that may or may not be chaotropic can be used in conjunction with sulfolane to bind nucleic acids to at least one mineral support. Under these conditions, proteins will not bind to any appreciable extent, and can thus be captured in flow-through or eluate fractions, free or essentially free of one or more nucleic acids. For some proteins and protein analysis techniques (e.g., enzyme activity assays), the conditions for binding should be such that the protein of interest is not denatured or otherwise non-reversibly altered in tertiary or quaternary structure. However, for some proteins, denaturation is acceptable if renaturation may be accomplished without significant detriment to the structure or activity of the protein. Also, compositions comprising proteins that do not bind to a mineral support in the presence of sulfolane, alone or in the presence of one or more salts, can be exposed to the mineral support so that DNA and/or RNA is adsorbed. The protein of interest will flow through and can then be purified using protein purification methods known to those of skill in the art (for example, using ion exchange chromatography, hydrophobic interaction chromatography, etc.).

It was found, surprisingly, that sulfolane, in the presence of chaotropic salts, aids in the binding of nucleic acids in a sample to a substrate comprising, for example, glass, silica, or forms thereof. Sulfolane, an industrial chemical with the formula $C_4H_8O_2S$ (see FIG. 1), is also known by many other names, such as 2,3,4,5-tetrahydrothiophene-1,1-dioxide, sulpholane, tetrahydrothiophene-1,1-dioxide, tetramethylene sulfone, cyclic tetramethylene sulfone, cyclotetramethylene sulfone, sulfolan, thiophan sulfone, thiophene, sulfalone, among others. As all of these names are interchangeable and refer to the same chemical compound, the method of the present invention pertains to all of the names listed here, as well as other names not listed but with the same structure as seen in FIG. 1. For ease of reference, herein, the term sulfolane will be used. One can also envision that compounds with substitutions and additions at the carbon atoms of sulfolane may also perform as sulfolane in terms of allowing binding of biological molecules to at least one mineral support. For example, one or more of the carbons of the 5-membered ring may be substituted with short chain alkyl groups, such as methyl, ethyl, propyl, isopropyl, butyl, pentyl, hexyl, septyl, and octyl. Likewise, hydroxyl substitutions may be permitted at one or more of the carbons, as can carboxyl and carbonyl groups. Nitrogen-containing, sulfur-containing, and oxygen-containing groups may be substituted on one or more carbons as well. However, a modification of sulfolane that prevents miscibility with water may not allow good binding of biological molecules to a mineral support, and therefore may not be as advantageous in the method of this invention.

As used herein, the term "biological molecule" refers to any molecule found within a cell or produced by a living organism, including viruses. This may include, but is not limited to, nucleic acids, proteins, carbohydrates, and lipids. In preferred embodiments, a biological molecule refers to a nucleic acid or a protein, and most preferably to a nucleic acid. A biological molecule can be isolated from various samples such as tissues of all kinds, cultured cells, body fluids, whole blood, blood serum, plasma, urine, feces, microorganisms, viruses, plants, and mixtures comprising nucleic acids following enzyme reactions. Examples of tissues include tissue from invertebrates, such as insects and mollusks, vertebrates such as fish, amphibians, reptiles, birds, and mammals such as humans, rats, dogs, cats and mice. Cultured cells can be from procaryotes such as bacteria, blue-green algae, actinomycetes, and mycoplasma and from eucaryotes such as plants, animals, fungi, and protozoa. The methods of this invention can be employed for extremely small samples of cells, such as 1-$10^4$ cultured cells or fewer, or cells harvested by laser capture microdissection. Blood samples include blood taken directly from an organism or blood that has been filtered in some way to remove some elements such as red blood cells, and/or serum or plasma. Nucleic acid can be isolated from enzyme reactions to purify the nucleic acid from enzymes such as DNA polymerase, RNA polymerase, reverse transcriptase, ligases, restriction enzymes, DNase, RNase, nucleases, proteases etc. or any other enzyme that can contact nucleic acids in a molecular biology method.

In a preferred method of the invention, single-stranded RNA is separated from double-stranded nucleic acid, preferably DNA. If DNA is present in a single-stranded form, it may be separated from double-stranded DNA, as well as from double-stranded RNA. RNA that can be isolated by this method includes mRNA, tRNA, rRNA and noncoding RNA such as snRNA, snoRNA, miRNA, and siRNA. The size of RNA that can be isolated by this method is not particularly limited, but typically ranges from about 20 nucleotides (such as some siRNA) to more than about 5 kb or 6 kb (such as some mRNA).

The terms "isolated" and "purified" mean that the biological molecule is separated from other substances in the sample. These substances may include different types of molecules as compared to the molecule that is being isolated. For example, nucleic acids may be isolated from other biological molecules such as proteins, carbohydrates, and lipids, and any other molecule found in cells. Substances may also refer to the same type of molecule as compared to the molecule that is being isolated. For example, one specific protein may be isolated from other proteins or one kind of nucleic acid may be purified away from other types of nucleic acids. The biological molecule may also be separated from other substances such as debris from lysed or sheared cells or tissue components such as cellular organelles and connective tissue. Substances may also include whatever buffer or liquid the cells or tissue were in such as a lysis buffer or media for growing cultured cells. The biological molecule can be partially purified with the methods of this invention such that it is partially separated or partially purified from some of the other substances in the sample. The biological molecule can be mostly purified such that it is more than 80% pure. It can also be pure or almost pure such that at least 95%, such as 98%, 99%, 99.5%, or greater of the biological material in the final elution comprises the biological molecule of interest. Of course, any level of isolation or purity is envisioned by this invention, from 1% to 100%, and all of the particular values within this range, including fractions thereof, are contemplated, and it is to be understood that those of skill in the art will immediately recognize each particular value within the range without each particular value needing to be recited specifically herein. As used herein, isolated and purified are used interchangeably.

In embodiments, such as when the method is practiced with a sample that is solid tissue, the method of the invention comprises combining the sample with high concentrations of salt before adsorbing the sample onto the mineral substrate. Combining can be any action that results in the sample and salt coming into contact. Combining may be done by adding a lysis buffer comprising high salt to the sample. For isolation of nucleic acids, preferably, the salts in the lysis buffer are chaotropic salts found in a concentration from about 0.1 to about 10 M, such as from about 1 to about 5 M or from about 5 to about 10 M. In a preferred embodiment, 4 to 5 M salt is used in the lysis buffer. The salts used in these methods may be chaotropic salts, such as guanidinium chloride, guanidinium thiocyanate, guanidinium isothiocyanate, sodium perchlorate, and sodium iodide. Non-chaotropic salts include salts of Group I alkali metals, such as sodium chloride, sodium acetate, potassium iodide, lithium chloride, potassium chloride, and rubidium and cesium based salts. As a general matter, any salt that will allow the binding of a biological molecule to the mineral substrate in the presence of sulfolane may be used in this method. The salts in the invention may be one particular salt or may comprise combinations thereof such that a mixture of salts are used. Urea, another chaotropic substance, in concentrations from 0.1 to 10 M may also be used for lysing and/or binding the sources containing the biological molecules. In one embodiment, sarkosyl (preferably 0.05%) is added to the lysis buffer to reduce double-stranded nucleic acid content when single-stranded nucleic acid is being isolated.

As can be seen from the above disclosure, in embodiments, a composition comprising one or more salts may be a composition for lysis of a cell. Alternatively or additionally, for samples comprising intact cells, the cells can be lysed by mechanical ation, such as by using a homogenizer (for example, rotating blade, mini-, or micro Dounce), a laboratory vortexer, repeated pipetting, or any other method that aids in lysing the cells. Some cells cannot be lysed directly in aqueous buffers containing chaotropic salts (e.g., bacteria, due to their cell walls). Therefore, some samples can be pretreated, for example, with lytic enzymes, as part of a method of the invention.

After optional lysis of the cells in a sample, the sample can optionally be prefiltered through a prefiltration substrate. Among other things, this step minimizes the clogging of the mineral substrate and allows biological molecules from a larger number of cells to be added to the mineral substrate. For example, prefiltering allows at least $1 \times 10^8$ cells to be processed on a single mineral support. Among the many examples possible, up to $1 \times 10^8$ or more cultured cells can be processed, and at least $1 \times 10^7$ (e.g., $5 \times 10^7$) white blood cells can be processed on a mineral support designed for lab-bench scale processing, such as commercial filter holders accommodating glass fiber disks of 47 mm diameter. In embodiments, up to 40 mg or more of solid tissue can be used. The substrate utilized for the prefilter step can be any material that retains larger particles, such as cellular debris from lysis or genomic double-stranded nucleic acid, but allows smaller biological molecules to pass through the prefiltration substrate. The substrate for prefiltration preferably may include a single or a combination of materials such as porous polyethylene frits, glass fiber, and cellulose acetate. In the case where the biological molecule being isolated is a single-stranded nucleic acid, the preferred materials can be used in a variety of configurations and combinations because of high retentive capacity for larger particles and inability to bind single-stranded nucleic acid to any great extent in the absence of a chaotropic salt and an organic solvent, such as ethanol, acetonitrile, tetrahydrofuran, acetone, 1,3-dioxolane, sulfolane, etc. The prefiltration substrates can be provided in any shape or size. For example, they can be provided in a combination of filter and an insert (collar) or polyethylene frit, which can be used for retaining the filter and, in embodiments, providing a filtering function. In embodiments, the system comprises one or more prefiltration spin cups (such as those available in the Stratagene Absolutely RNA Miniprep system) that comprise two 10 micrometer pore size polyethylene frits, eight layers of glass fiber, and a 0.45 micrometer pore size cellulose acetate filter. Of course, any number of configurations and combinations can be used for the prefilter as long as double-stranded molecules such as DNA are retained and single-stranded molecules such as RNA flow through the prefilter. In some embodiments, the prefilter comprises one or more (e.g., two, three, four, etc.) glass filters, such as Whatman GF/D, or Ahlstrom Paper Group (Mount Holly, Pa.) 121 filters.

The step of prefiltration comprises contacting the sample comprising at least one biological molecule with a prefiltration substrate for a sufficient amount of time and under appropriate conditions to allow for capture of at least one biological molecule in the sample by the prefilter. The step also comprises separating the unbound sample from the prefiltration substrate and bound biological molecule(s). Separation of the remaining sample from the prefiltration substrate comprising at least one biological molecule can occur using any suitable technique, including, but not limited to, gravity, centrifugation, positive air pressure, and/or vacuum etc. Methods of separation are well known in the art and therefore will not be described in detail herein.

In some embodiments, the methods of the invention comprise exposing the flow-through fraction (eluate) to a second substance that binds biological molecules, such as a mineral support or substrate that binds nucleic acids. The method may comprise combining the sample eluted from the prefiltration substrate with sulfolane before exposing the resulting sample to the mineral substrate under conditions wherein the biological molecule of interest binds to the substrate. In these embodiments, the sulfolane is typically added after prefiltration of the sample. The final concentration of sulfolane may be any amount that allows for binding of the molecule of interest. For nucleic acids, it can range from 0% to 100%, such as from 15% to 80%, for example from 20% to 50%. In embodiments where the target molecule is RNA, a final concentration of about 15% to about 45% (e.g., 35%, 36%, 37%, 38%, 39%, 40%) sulfolane is typically employed for the method to maximize RNA binding. In embodiments where low molecular weight double- and single-stranded nucleic acids are the target molecules, a final concentration of greater than 40% can be used. While not being limited to any one mode of action, it is envisioned that concentrations of sulfolane between about 35% and about 45% favor binding of RNA, whereas relatively high concentrations of sulfolane permit binding of low molecular weight double- and single-stranded nucleic acids. Preferably, the purity of the sulfolane is about 98% or greater, for example 99.5% or 99.8%. Sulfolane of such purity is commercially available, for example from Aldrich or Fluka.

The mineral substrate used for adsorbing the biological molecule preferably consists of or comprises porous or nonporous metal oxides or mixed metal oxides, silica gel, sand, diatomaceous earth, materials predominantly consisting of glass, such as unmodified glass particles, powdered glass, quartz, alumina, zeolites, titanium dioxide, and zirconium dioxide. Fiber filters comprised of glass or any other material that can be molded into a fiber filter may be employed in this method. If alkaline earth metals are used in the mineral substrate, they may be bound by ethylenediaminetetraacetic acid (EDTA) or EGTA, and a sarcosinate may be used as a wetting, washing, or dispersing agent. Any of the materials used for the mineral substrate may also be engineered to have magnetic properties. The particle size of the mineral substrate is preferably from 0.1 um to 1000 um, and the pore size is preferably from 2 to 1000 um. The mineral substrate may be found loose, in filter layers made of glass, quartz, or ceramics, in membranes in which silica gel is arranged, in particles, in fibers, in fabrics of quartz and glass wool, in latex particles, or in frit materials such as polyethylene, polypropylene, and polyvinylidene fluoride. The mineral substrate may be in the form of a solid such as a powder or it may be in a suspension of solid and liquid when it is combined with a liquid sample. The mineral substrate can be found in layers wherein one or more layers are used together to adsorb the sample. In one embodiment, the mineral substrate is found packed into a spin column or spin cup that can be placed in a microcentrifuge tube. In another embodiment, the mineral substrate is packed into a bigger spin column or spin cup for biological molecule isolation from larger samples. In still another embodiment, the mineral substrate is not packed but is found loose and is mixed with the sample. The mineral substrate can also be found in a filter housing allowing fluids to be passed through by positive air pressure and/or vacuum etc. The methods of the invention can be used for high-throughput and/or automated purification wherein biological molecules are isolated from many samples. For example, the mineral substrate can be found in a 96-well binding plate.

The step of adsorbing the biological molecule to the mineral substrate comprises contacting or treating a sample comprising at least one biological molecule to be separated with at least one mineral substrate, in the presence of an appropriate mixture of salts and sulfolane (e.g., an aqueous solution) such that at least some of the biological molecule is adsorbed on the mineral substrate. Contacting of the substrate and sample can occur by any means that will bring the sample together with the substrate, such as a laboratory vortexer, shaker, repeated pipetting, diffusion between the substrate molecules and the sample molecules, centrifugation, positive air pressure, and/or vacuum. Adsorption of the biological molecule onto the mineral substrate can be performed by gravity, centrifugation, positive air pressure, and/or vacuum, simple diffusion, etc.

In a preferred embodiment, the biological molecule being isolated is RNA. When the RNA and the mineral substrate, which is preferably silica-based such as one or more glass filters, are exposed to each other in the presence of a chaotropic and/or other useful salt as previously described and an adequate amount of sulfolane, the majority of the RNA becomes bound to the mineral substrate. In this context, the term "majority" means that more than 50.1% of the RNA molecules are bound to the mineral substrate, such as in some cases, more than 80% and in other cases, more than 90%. As mentioned above, those of skill in the art can immediately recognize all of the particular values encompassed by this range, and thus each particular value need not be specifically recited herein.

Once at least one biological molecule has been adsorbed to the mineral substrate, the substrate can be optionally washed at least once with one or more solutions that contain an organic solvent, such as ethanol, an organic solvent similar to ethanol, or mixtures thereof. An organic solvent similar to ethanol means a solvent of "like" chemical and physical properties. For example, the solvent may have similar specific gravity, miscibility in water, or other characteristics that allow it to be a component of the wash buffer without removing the biological molecule from the mineral substrate. "Mixtures thereof" means that more than one kind of organic solvent may be used in the wash buffer. For example, a mixture of ethanol and sulfolane, a mixture of sulfolane and dioxolane, ethanol and dioxolane, ethanol, sulfolane, and acetonitrile, etc. may be used for washing the mineral substrate. There are many variations of mixtures of organic solvents that can be used for this step and the mixture may comprise more than two organic solvents. The wash solution may also comprise one or more salts. If salt is used in the wash solutions, the salt may be a chaotropic salt or a salt comprising an alkaline metal (e.g., a Group I metal, such as sodium chloride) or alkaline earth metals (e.g., a Group II metal salt). The salt concentration can range from 0.001 M to 3 M. Likewise, the organic solvent may range from a final concentration of 1% or less to 100% by volume. For example, the organic solvent may be present in a final concentration of approximately 50%. Thus, the range of salt and ethanol and/or other solvent concentrations in the salt solution can be from no salt and 100% total solvent to 3 M salt and about 80% total solvent or less. In some embodiments, the solution is a high salt buffer comprising one or more organic solvents (e.g., 10-90% by volume) and having a salt content of about 50 mM or greater. In other embodiments, the solution is a low salt buffer comprising one or more organic solvents (e.g., 10-90% by volume) and having a salt content of less than about 50 mM, such as one comprised of 20 mM NaCl and from about 50% to about 60% ethanol (e.g., about 52%, 54%, 56%, 58%). Methods of washing are well known in the art (such as adding the buffer to the sample and then centrifuging the sample or applying positive air pressure and/or vacuum to the sample) and therefore will not be described in detail herein. Any suitable washing scheme may be used. Where high salt and low salt washing buffers are used, it is preferable that the high salt wash be performed first, as a goal of the washing is to remove unwanted biological materials. The high salt wash is followed by the low salt wash to reduce the amount of salt associated with the bound material.

Thus, before elution of the biological molecules from the mineral substrate, the substrate can be treated with one or more high salt or low salt washes to remove contaminating proteins, including DNase or RNase. The high salt wash is comprised of, for example, 1 to 8 M salt and 20% to 80% ethanol or other organic solvent, or a mixture of solvents. In a preferred embodiment, the high salt wash is comprised of 2 M chaotropic salt and about 50% to about 60% ethanol. This optional high salt wash step can incorporate one or more high salt washes. In a preferred embodiment, when RNA is being isolated and a DNase step is used, two or three high salt washes are performed comprising 2 M guanidinium thiocyanate and about 50% to about 60% ethanol or solvents of "like" physical and chemical properties. Where desired, a low salt solution, such as that described above, can be used after the high salt washes to lower the salt concentration of the nucleic acid containing composition.

After the optional high and/or low salt washes, the mineral substrate can be treated with DNase, RNase, proteases, or other enzymes in an appropriate aqueous environment to remove biological compounds that are not of interest. In one preferred embodiment, RNA is the biological molecule of interest and a DNase digestion buffer is added to eliminate DNA molecules from the mineral substrate. In another embodiment, DNA is the molecule of interest and an RNase digestion buffer is added to eliminate RNA molecules from the mineral substrate. Following DNase or RNase treatment, the mineral support is washed with high salt and low salt washing buffers, respectively, to remove residual DNase, RNase, or salts.

The step of eluting the biological molecules from the mineral substrate can comprise first drying (e.g., by simple evaporation in air) the mineral substrate to eliminate water and the organic solvent (e.g., ethanol), then adding a liquid, such as elution buffer or water, to the substrate, optionally allowing the liquid to incubate with the substrate from zero to one hour or more, and separating the liquid from the substrate. Under some circumstances, the bound biological molecules can be exposed to a highly volatile organic compound, such as acetone, to facilitate removal of water and other organic compounds by evaporation. In embodiments where nucleic acids are being eluted, incubation typically can occur from about zero seconds to about 20 minutes, such as from about zero seconds to about 10 minutes, or from about zero to about 5 minutes. In a preferred embodiment, incubation occurs for about 2 minutes. During this step, most of the nucleic acid molecules bound to the substrate should elute into the liquid. Incubation can occur with a liquid that is warm, such as from about 26° C. to about 80° C. or close to room temperature, such as from about 20° C. to about 25° C. Preferably, where the elution solution (e.g., buffer) comprises salts, the salts have a pKa value from about 6 to about 10 and the buffer has a salt concentration up to about 100 mM. For example, 10 mM Tris (pKa 8.0) pH 8.5 may be used to elute the biological molecule from the mineral substrate.

Thus, in embodiments, the invention provides a process for the separation of single-stranded nucleic acids from double-stranded nucleic acids by treatment of a biological source, where the treatment comprises: a) applying to a first mineral support an aqueous sample comprising material of the source under conditions whereby the first mineral support adsorbs or binds only one of the single- or double-stranded nucleic acids followed by, optionally, washing the first mineral support; and b) applying to a second mineral support the other of the single- or double-stranded nucleic acids, which was not adsorbed or bound by the first mineral support, in an aqueous solution containing sulfolane. In the process, the applying step to the first mineral support can comprise adding to the aqueous sample salts and sulfolane in amounts such that the single-stranded, but not the double stranded, nucleic acids are adsorbed on or bound to the first mineral support, followed by, optionally, washing of the first mineral support. In addition, the double-stranded nucleic acids, which were not adsorbed on or bound to the first mineral support, can be applied to the second mineral support in the presence of appropriate amounts of one or more salts and sulfolane such that the double-stranded nucleic acids are adsorbed on or bound to the second mineral support, followed by, optionally, washing of the second mineral support. Further, the single-stranded nucleic acids, double-stranded nucleic acids, or both can be eluted from the first and second mineral supports, respectively. According to the process, the applying step to the first mineral support can comprise adding the aqueous sample to materials that complex alkaline-earth metal ions, in the absence of sulfolane, such that double-stranded, but not single-stranded nucleic acids are adsorbed on or bound to the first mineral support. The single-stranded nucleic acids, which were not adsorbed on or bound to said first mineral support, can be applied to the second mineral support in the presence of salts and sulfolane in amounts such that the single-stranded nucleic acids are adsorbed on or bound to the second mineral support, followed by optionally, washing of the second mineral support. Further, the double-stranded nucleic acids, single-stranded nucleic acids, or both can be eluted from the first and second mineral supports, respectively.

In some instances, the process can be characterized by the applying step to the first mineral support comprising adding to the aqueous sample wetting, washing, or dispersing agents, in the absence of sulfolane, such that the double-stranded nucleic acids are adsorbed on or bound to the first mineral support, followed by, washing of the first mineral support. In addition, the single-stranded nucleic acids, which were not adsorbed on or bound to the first mineral support, can be applied to the second mineral support in the presence of sulfolane in amounts such that the single-stranded nucleic acids are adsorbed on or bound to the second mineral support, followed by optionally, washing of the second mineral support. Further, the single-stranded, double-stranded nucleic acids, or both can be eluted from the first and second mineral supports, respectively. In some embodiments, the applying step to the first mineral support comprises adding to the aqueous sample salts and sulfolane in amounts such that both the single-stranded and double-stranded nucleic acids are adsorbed on or bound to the first mineral support, one of the single- or double-stranded nucleic acids is, selectively, first eluted from the first mineral support, followed by eluting the other of the single- or double-stranded nucleic acids, and the one of the single- or double-stranded nucleic acids, which was first eluted from the first mineral support, is applied to the second mineral support under conditions whereby the nucleic acids first eluted from the first mineral support are adsorbed on or bound to the second mineral support, followed by eluting the nucleic acids from the second mineral support.

As mentioned above, in the method or process of the invention, salts can be present in concentrations of from 1 to 10 M. For example, the process or method can comprise, prior to applying a sample to a first mineral support, lysing cells in a source containing the nucleic acids with chaotropic substances present in concentrations of from 0.1 to 10 M. To reiterate, in the processes and methods of the invention, sulfolane can be present in concentrations of from 1 to 90% by volume, final concentration. In addition, the make-up of the first and second mineral supports is not particularly limited, and thus can be, independently, for example, porous or non-porous and comprised of metal oxides or mixed metal oxides, silica gel, glass particles, powdered glass, quartz, alumina, zeolites, titanium dioxide, or zirconium dioxide. The particle size of the mineral supports is likewise not limited, and can be, for example, from 0.1 micrometers to 1000 micrometers. Further, the pore size of porous mineral supports is not limited, and can be, for example, from 2 to 1000 micrometers. Complexes formed in the process can comprise alkaline earth metal ions bound to ethylenediaminetetraacetic acid (EDTA) or EGTA. Furthermore, where a wetting, washing, or dispersing agent is used in one or more lysing, binding, or washing solutions, the wetting, washing or dispersing agent can be a sarcosinate.

In another general aspect, compositions comprising sulfolane and another substance are provided. In general, a composition of the invention comprises sulfolane and at least one biological molecule, such as a double-stranded nucleic acid (e.g., DNA), a single-stranded nucleic acid (e.g., RNA), or a protein, polypeptide, or peptide. In some embodiments, the compositions comprises a sufficient amount of sulfolane and sufficiently high concentrations of at least one salt to isolate at least one biological molecule. For example, there could be a sufficient amount of each to cause RNA to bind to a glass fiber, such as a filter. Various ranges of sulfolane that are useful in the methods of the invention, and thus the compositions of the invention, are disclosed above, and any of those ranges or particular concentrations may be used in a composition of the invention. In addition, various salts and concentrations of salts are discussed in the context of the methods of the invention above. Any of those salts, combinations of salts, ranges, or particular concentrations may be used in a composition of the invention. In embodiments, the composition comprises sulfolane and a high concentration of salt, which may be found in an aqueous buffer, such as a cell lysis buffer for lysis of one or more cells. In preferred embodiments for isolating nucleic acids from cells, the composition comprises 40% sulfolane and 4 to 5 M chaotropic salt in a cell lysis buffer. In addition, the various types and amounts of mineral supports that may be present in the compositions are disclosed herein.

Certain other aspects of the invention provide for use in the preparation of compositions for biotechnology research use. For example, in some embodiments the invention provides for the use of sulfolane in the preparation, isolation, purification, etc. of a biological molecule, and preferably a nucleic acid such as RNA or DNA. Compositions may comprise substances of the invention along with one or more other substances, which are typically substances that are commonly used in biotechnology. In some embodiments, the compositions comprise cell lysate. In others, the compositions comprise one or more biological molecule, such as a nucleic acid, a protein, a carbohydrate, or a lipid. Where the composition comprises a nucleic acid, it can comprise RNA, DNA, or both. It likewise can contain single-stranded nucleic acids, double-stranded nucleic acids, or both. In addition, compositions of the invention can comprise cell lysate or a portion of cell lysate.

In yet another general aspect, the present invention provides kits. In general, the kits comprise packaging for holding one or more containers. Typically, the containers contain at least one reagent, supply, or material for practicing a method of the invention. In preferred embodiments, the kit comprises sulfolane. For example, a kit can comprise sulfolane and a salt (present as a dried salt or in a liquid composition), which, when combined, facilitate binding of a biological molecule to a mineral support. Thus, the kit may comprise a container (e.g., tube, vial, ampule) that holds a mixture of sulfolane and salt, which can be used to isolate at least one biological molecule, preferably a nucleic acid molecule. Alternatively, the sulfolane and salt may be stored in separate containers and mixed at the appropriate time. Often, the kit of the invention will comprise a composition of the invention, which is supplied in the kit in one or more containers, each container independently containing sulfolane, salt, or a combination of the two. In embodiments, the kit comprises one or more containers holding an appropriate mix of sulfolane and salt to isolate at least one nucleic acid molecule. The kits can comprise other components, such as some or all of the components necessary to practice a method of the invention. For example, the kits may comprise one or more filters or filter units, such as prefilters. It likewise may comprise one or more mineral substrates or substrate units (e.g., multiple layers of mineral substrates provided as a single unit). Additionally, the kit may comprise the filters or mineral substrates in a form for immediate use, such as fashioned within a tube for performing an isolation using gravity or centrifugation. In another example, the mineral substrate may be in the form of beads, either non-magnetic or magnetic. Other non-limiting examples of components that may be included in the kits of the invention are sterile water, cell lysis buffer, wash buffers, and elution buffers or water. Of course, multiple organic solvents may be provided, independently or in mixtures of sulfolane and like solvents.

EXAMPLES

The invention will be further explained by the following Examples, which are intended to be purely exemplary of the invention, and should not be considered as limiting the invention in any way.

Example 1

Effect of Sulfolane on Purification of RNA from Jurkat Cells

RNA was isolated from a Jurkat cell line using the following protocol. Cultured cells ($2 \times 10^7$) were collected in a centrifuge tube and washed with PBS buffer (GIBCO formulation). The cells were resuspended in 10 ml of PBS and passed through two GF/D filters (47 mm diameter each) to capture the cells. The filters were washed with 20 ml of PBS to further reduce contaminants. Nine ml of White Blood Cell (WBC) Lysis Solution (4 M guanidine thiocyanate, 1% Triton X-100, 0.05% sarkosyl, 0.01% Antifoam A, 0.7% beta-mercaptoethanol) was passed through the filters resulting in the release of nucleic acids from the cells and the lysate was collected comprising mostly RNA. The genomic DNA was retained on the GF/D filters and could be physically and/or chemically retrieved later. Four ml of water was passed through the GF/D filters to release additional RNA and this fraction was added to the WBC lysate. In the standard protocol, 13 ml of 80% sulfolane was added to the total lysate fraction for a final sulfolane concentration of 40%. In this experiment, sulfolane was adjusted to a final concentration of 10% to 45% to determine the effect of different concentrations of sulfolane. In addition, in some samples, ethanol at a final concentration of 35% was substituted for sulfolane to compare the two solvents. The resulting mixture was passed over five GF/F filters (9.5 mm diameter each). The GF/F filters were washed three times with 2.5 ml of Low Salt Wash Solution (2 mM Tris (pH 6-6.5), 20 mM NaCl, 80% ethanol) for a total of 7.5 ml. The filters were purged of excess liquid between each addition of Low Salt Wash Solution and after the final addition, the filters were air dried. The RNA was eluted from the GF/F filters with 100 ul (microliters) of RNase-free water. The eluted RNA was checked for yield by measuring absorbance on a spectrophotometer at $A_{260}$ and purity was checked using the $A_{260}/A_{280}$ ratio.

Figures 3C, 3D:
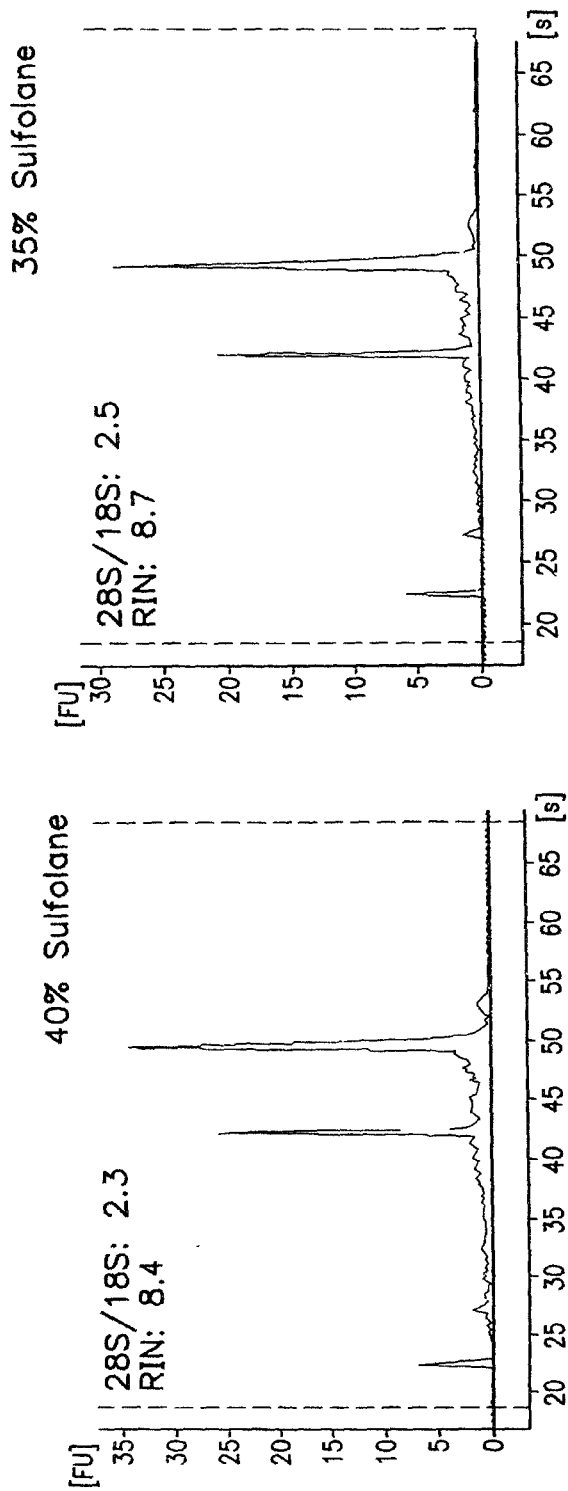
FIG. 3 depicts the quality of RNA isolated from Jurkat cells as seen by data from an Agilent Bioanalyzer.

Results from this experiment can be seen in Table 1. Sulfolane concentrations of 40% and 45% resulted in equivalent RNA yield and purity when compared to an ethanol concentration of 35%. Agilent Bioanalyzer traces (FIG. 3) demonstrated that 35% ethanol compares favorably with 45% sulfolane with respect to RIN number and 28/18 S ribosomal RNA ratios. More specifically, as shown in FIG. 3A, RNA isolated using 35% ethanol had a 28S/18S ratio of 2.0 and an RNA Integrity Number (RIN) of 7.9. In comparison, FIGS. 3B, 3C, and 3D show that RNA isolated using 45%, 40%, and 35% sulfolane in the RNA binding buffer, respectively, has an even higher 28S/18S ratio (2.1, 2.3, and 2.5, correspondingly) and higher RIN (7.9, 8.4, and 8.7, correspondingly). In summary, RIN number and 28/18 S ribosomal RNA ratio in the sulfolane series increase in the following order: 45% sulfolane (RIN=7.9; 28/18 S=2.0); 40% sulfolane (RIN=8.4; 28/18 S=2.3); and 35% sulfolane (RIN=8.7; 28/18 S=2.5). Overall, RNA isolated using either ethanol or sulfolane had a very good quality.

Figure 4:
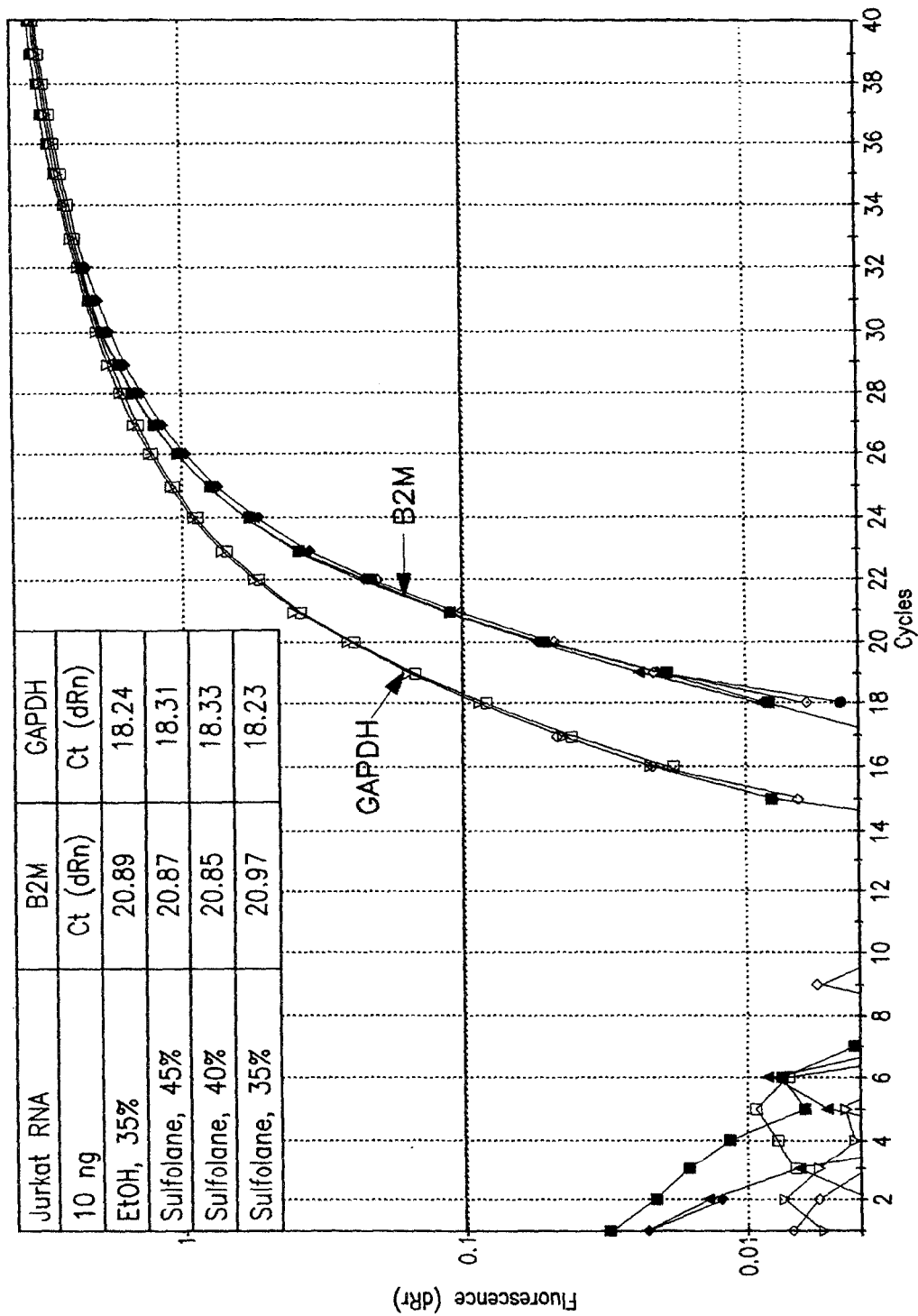
FIG. 4 depicts the quality of RNA isolated from Jurkat cells as seen by data from QRT-PCR using a Stratagene Mx 3000P Real-Time PCR instrument.

Evaluation of RNA quality by reverse transcription and amplification of beta-2-microglobulin (B2M) and glyceraldehyde-3-phosphate dehydrogenase (GAPDH) mRNA using Quantitative Real Time PCR (QRT-PCR) also showed equivalent RNA quality when isolated using 45%, 40%, and 35% sulfolane and 35% ethanol (FIG. 4). More specifically, FIG. 4 shows amplification plots of Real-time QRT-PCR reactions that were performed using 10 ng of each RNA (25 ul reaction volume), Brilliant QRT-PCR Master Mix, 1-step (Stratagene) and TaqMan primers and probe (B2M and GAPDH, Assay on Demand, ABI) on the Mx3000P Real-time PCR System (Stratagene) using the following cycling parameters: 50°/30 min, then 95°/10 min followed by 40 cycles of 95°/15 sec; 60°/1 min. Primers used were from the ABI system. All four RNA samples showed very similar Cts for two tested genes and perfect amplification curves overlapping, suggesting that all four tested RNA samples isolated either with ethanol or 35%-45% sulfolane have an equally high quality.

TABLE 1

| Jurkat cells | EtOH | Sulfolane | RNA, ng/ul | A260/280 |
|---|---|---|---|---|
| 1 | 35% |  | 65.81 | 2.1 |
| 2 | 35% |  | 67.3 | 2.09 |
| 3 |  | 45% | 70.49 | 2.08 |
| 4 |  | 40% | 67.79 | 2.1 |
| 3 |  | 35% | 63.8 | 2.09 |
| 5 |  | 30% | 27.81 | 2.02 |
| 6 |  | 25% | 7.42 | 1.94 |
| 7 |  | 20% | 4.63 | 1.77 |
| 8 |  | 15% | 4.55 | 2.13 |
| 10 |  | 10% | 3.72 | 1.82 |

Example 2

Effect of Sulfolane on Purification of RNA from White Blood Cells

RNA was purified from white blood cells using a modification of the protocol described in Example 1. Five milliliters of blood, collected in a vacutainer tube with EDTA anticoagulant, was mixed with 20 ml Red Cell Lysis Solution (0.15 M ammonium chloride, 0.001 M potassium bicarbonate, 0.0001 M EDTA, pH 7.2-7.4) and incubated at room temperature for 5 minutes. White blood cells were collected by centrifugation and processed starting at the PBS buffer step as described in Example 1. Analysis of the RNA by UV spectrophotometry showed equivalent RNA yield and purity with 40% sulfolane and 35% ethanol (Table 2).

TABLE 2

| WBC | EtOH | Sulfolane | RNA, ng/ul | A260/280 |
|---|---|---|---|---|
| 1 | 35% |  | 12.26 | 2.04 |
| 2 | 35% |  | 9.87 | 2.24 |
| 3 |  | 40% | 11.32 | 2.25 |
| 4 |  | 40% | 12.02 | 1.99 |

Figure 5:
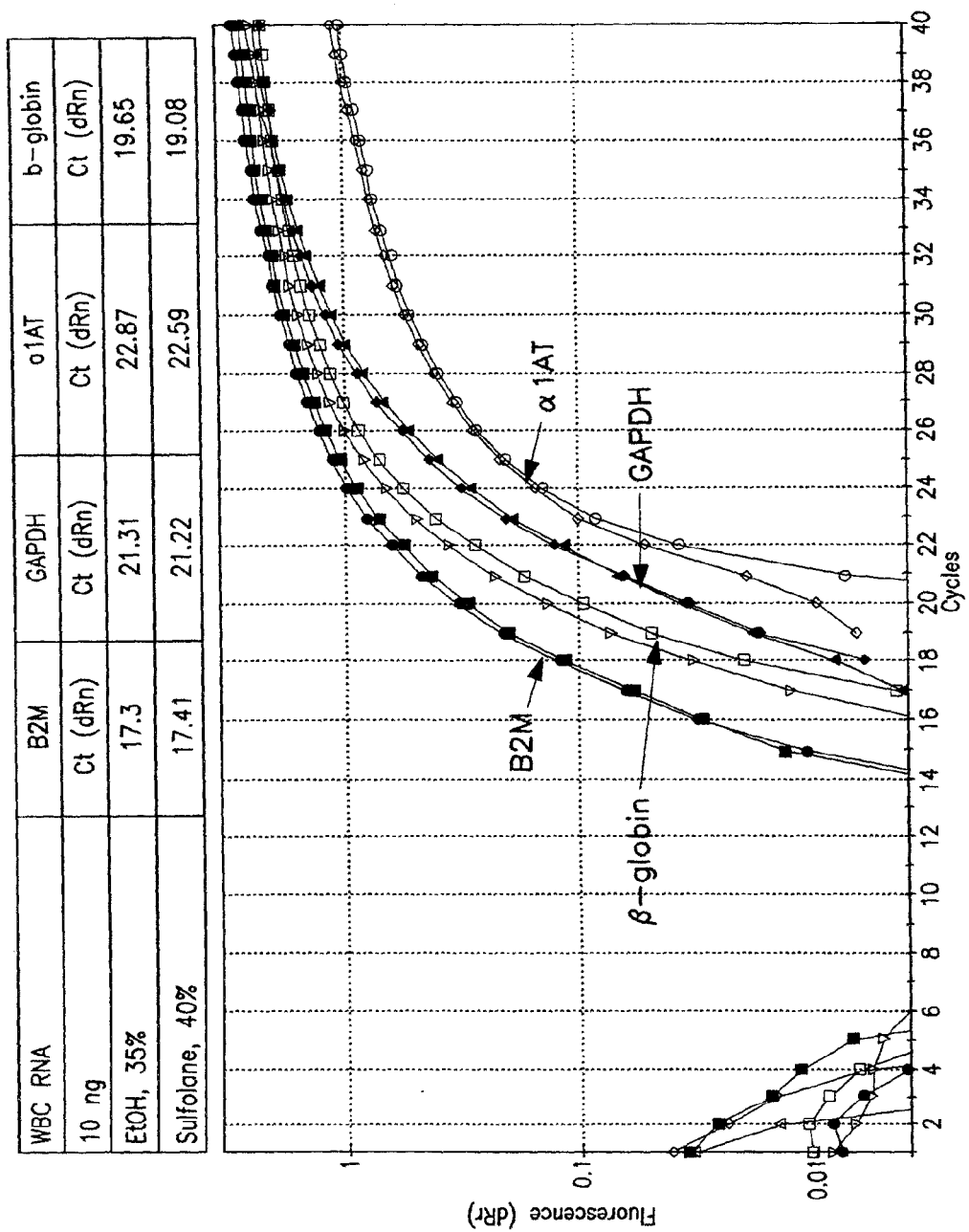
FIG. 5 depicts the quality of RNA isolated from white blood cells using the method described in Example 2 as seen by data from QRT-PCR using a Stratagene Mx 3000P Real-Time PCR instrument.

Evaluation of RNA quality by reverse transcription and amplification of beta-2-microglobulin (B2M), glyceraldehyde-3-phosphate dehydrogenase (GAPDH), beta-globin, and alpha-1 antitrypsin (alpha-1AT) mRNA using Quantitative Real Time PCR (QRT-PCR) also showed equivalent Ct values for each target, whether RNA was isolated using 40% sulfolane or 35% ethanol (FIG. 5). More specifically, FIG. 5 shows amplification plots of QRT-PCR reactions that were performed using 10 ng of each RNA (25 ul reaction volume), Brilliant QRT-PCR Master Mix, 1-step (Stratagene) and TaqMan primers and probe (B2M, GAPDH and alpha-1AT, Assay on Demand, ABI) and beta-globin TaqMan primers and probe set (beta-globin sense primer 5'-TGCACGTG-GATCCTGAGAACT-3' (SEQ ID NO: 1), beta-globin antisense primer 5'-AATTCTTTGCCAAAGTGATGGG-3' (SEQ ID NO:2), 5'-FAM/CAGCACGTTGCCCAGGAGC-CTG/3BHQ_1/-3'(SEQ ID NO:3) on the Mx3000P Real-time PCR System (Stratagene) using the following cycling parameters: 50°/30 min, then 95°/10 min followed by 40 cycles of 95°/15 sec; 60°/1 min. All four RNA samples showed very similar Cts for four tested genes and amplification curves that overlapped, suggesting that all four tested RNA samples had an equal quality. All examples and figures thus demonstrate that sulfolane is a functional substitute for ethanol, and in some cases provides higher quality purified nucleic acid than achieved using ethanol to adsorb the nucleic acids to mineral supports.

Example 3

Purification of RNA from Whole Blood

The standard protocol for purification of RNA from whole blood is described in this example. This standard protocol has been used to purify RNA from multiple samples (data not shown). Five ml of whole blood was added to 20 ml of Red Blood Cell (RBC) Lysis Solution (0.15 M ammonium chloride, 0.001 M potassium bicarbonate, 0.0001 M EDTA, pH 7.2-7.4). The sample was mixed and incubated for 5 min at room temperature. The resulting RBC lysate was passed through two 47 mm diameter GF/D filters to capture white blood cells and allow most plasma proteins and RBC contaminants to flow through the filters. The filters were washed with 20 ml of RBC Lysis Solution to further reduce contaminants. Nine ml WBC Lysis Solution (4 M guanidine thiocyanate, 1% Triton X-100, 0.05% sarkosyl, 0.01% Antifoam A, 0.7% beta-mercaptoethanol) was passed through the filters to release nucleic acids from the white blood cells, and the resulting lysate was collected comprising mostly RNA. Genomic DNA was retained on the GF/D filters and could be physically and/or chemically retrieved later. Four ml of water was passed through the GF/D filters to release additional RNA and this fraction was added to the WBC lysate. In the standard protocol, 13 ml of 80% sulfolane was added to the total lysate fraction for a final sulfolane concentration of 40%. The resulting mixture was passed over five GF/F filters (9.5 mm diameter each). The GF/F filters were washed three times with 2.5 ml of Low Salt Wash Solution (2 mM Tris (pH 6-6.5), 20 mM NaCl, 80% ethanol) for a total of 7.5 ml. The filters were air dried between each addition of Low Salt Wash Solution and after the final addition. The RNA was eluted from the GF/F filters with 100 ul (microliters) of RNase-free water. The eluted RNA was checked for yield and purity by UV spectrophotometry, Agilent Bioanalyzer traces, and QRT-PCR.

Analysis of the RNA by UV spectrophotometry showed similar RNA yield and purity when adding final percentages of 40% sulfolane and 35% ethanol to the cell lysate for RNA binding to the glass fiber in the spin cups (Table 3).

TABLE 3

| WBC | EtOH | Sulfolane | RNA, ng/ul | A260/280 |
| --- | --- | --- | --- | --- |
| 1 | 35% |  | 18.45 | 1.81 |
| 2 | 35% |  | 17.68 | 1.95 |
| 3 |  | 40% | 22.86 | 1.9 |
| 4 |  | 40% | 22.86 | 1.94 |

Figure 6A:
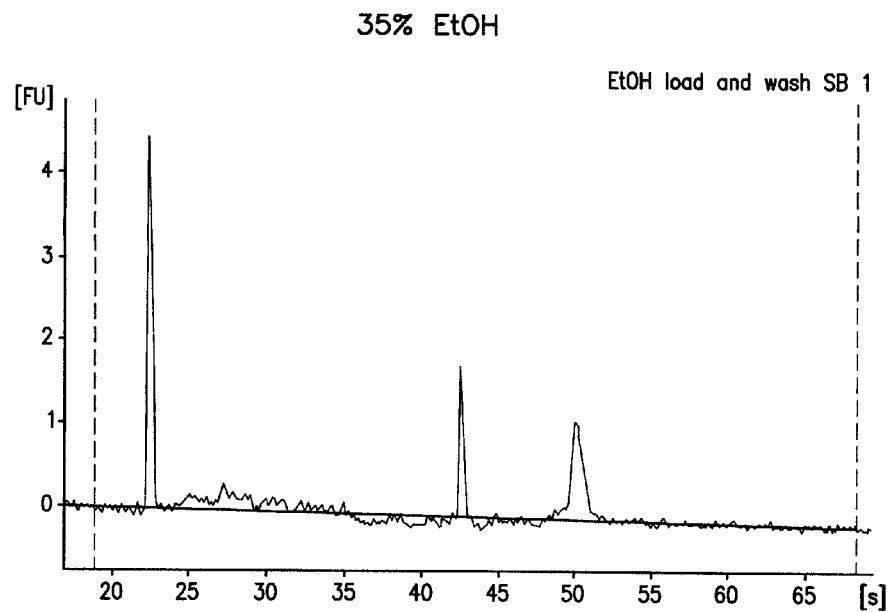
FIG. 6 depicts the quality of RNA isolated from white blood cells as seen by data from an Agilent Bioanalyzer.
Figure 6B:
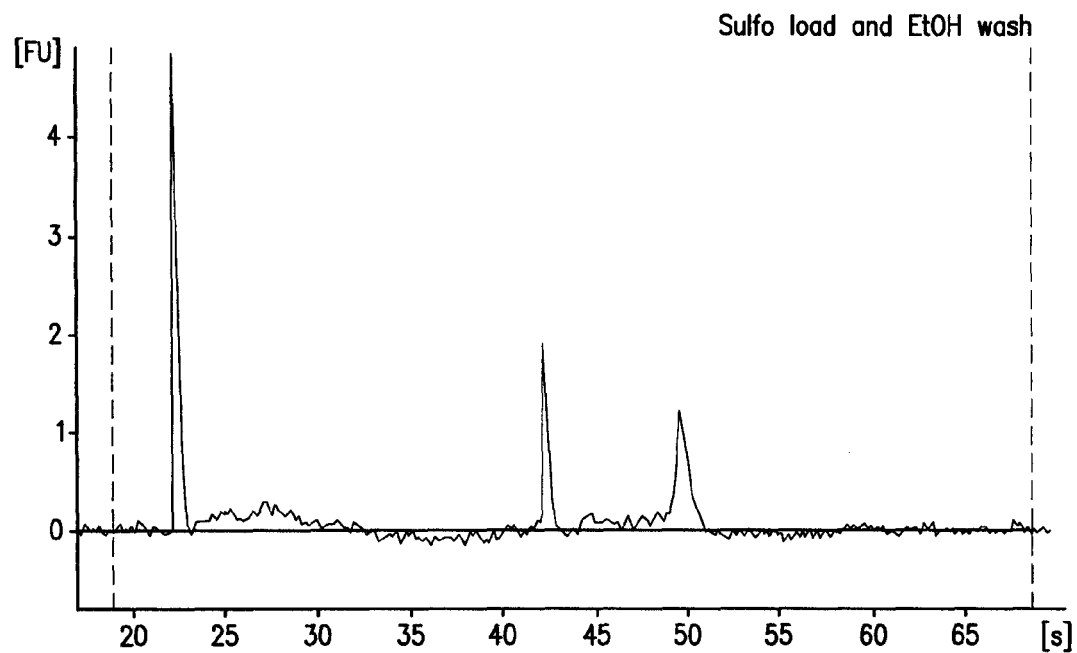

Agilent Bioanalyzer traces of RNA purified with final concentrations of 40% sulfolane and 35% ethanol were very similar, as shown in FIG. 6. More specifically, FIG. 6 shows that the Bioanalyzer traces for nucleic acids purified using 35% ethanol (Panel A) and 40% sulfolane (Panel B) are essentially superimposable, indicating that the quality of nucleic acid is essentially the same. In addition, RNA isolated with ethanol had a 28S/18S ratio of 1.2 and an RIN of 8.9, while RNA isolated using 45% sulfolane had a 28S/18S ratio of 1.1 and an RIN of 9.3.

Figure 7:
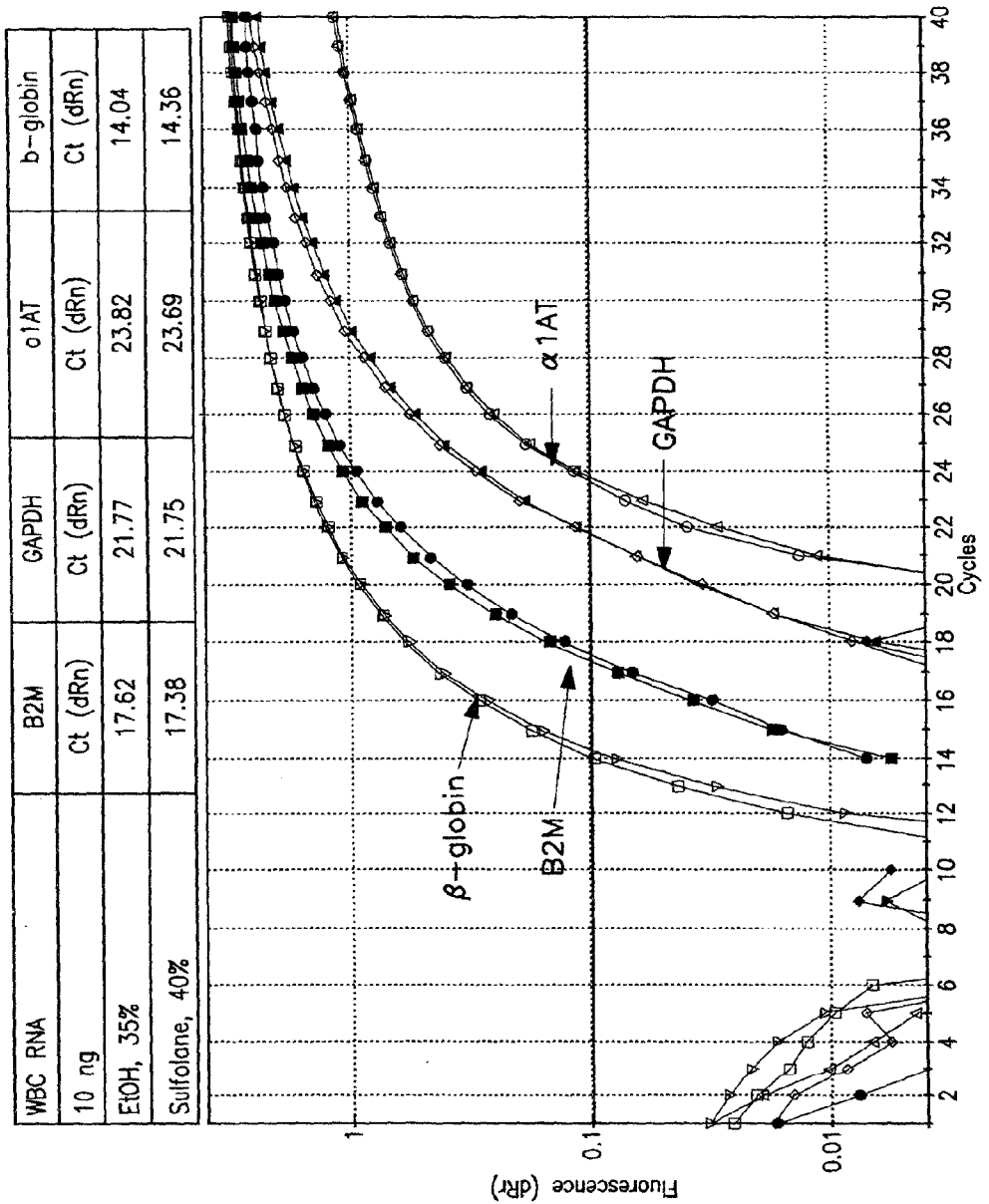
FIG. 7 depicts the quality of RNA isolated from white blood cells as seen by data from QRT-PCR using a Stratagene Mx 3000P Real-Time PCR instrument.

Evaluation of RNA quality by reverse transcription and amplification of B2M, GAPDH, beta-globin, and alpha-1AT mRNA using Quantitative Real Time PCR (QRT-PCR) showed equivalent quality of RNA when isolated using 40% sulfolane and 35% ethanol (see FIG. 7). It is to be noted that use of 45% final concentration sulfolane provides substantially equivalent results. More specifically, FIG. 7 shows amplification plots of QRT-PCR reactions that were performed using 10 ng of each RNA (25 ul reaction volume), Brilliant QRT-PCR Master Mix, 1-step (Stratagene) and TaqMan primers and probe (B2M, GAPDH and alpha-1AT, Assay on Demand, ABI) and beta-globin TaqMan primers and probe set (beta-globin sense primer 5'-TGCACGTG-GATCCTGAGAACT-3' (SEQ ID NO:1), beta-globin antisense primer 5'-AATTCTTTGCCAAAGTGATGGG-3' (SEQ ID NO:2), and probe 5'-/56-FAM/CAGCACGTTGC-CCAGGAGCCTG/3BHQ_1/-3' (SEQ ID NO:3) on the Mx3000P Real-time PCR System (Stratagene) using the following cycling parameters: 50°/30 min, then 95°/10 min followed by 40 cycles of 95°/15 sec; 60°/1 min. All four RNA samples showed very similar Cts for four tested genes and good amplification curves overlapping, suggesting that all four tested RNA samples had an equal quality. FIG. 7 and the data in it are in complete agreement with the data of the other examples and figures, and show that nucleic acids purified using sulfolane are essentially of the same purity as those purified using ethanol. Thus, again it is shown that sulfolane is a functional substitute for ethanol, and in some cases provides higher quality purified nucleic acid than achieved using ethanol to adsorb the nucleic acids to mineral supports.

Example 4

Preferential Binding of RNA to First Mineral Support

Varying binding conditions and wash conditions can be used to control whether RNA or DNA binds to and elutes from a first mineral support. The following guidelines provide parameters that can be used to preferentially bind RNA to the first mineral support.

Protocol:

Lyse cells in a lysis buffer containing 1-8 M chaotropic salt (e.g., 3.5 M guanidinium thiocyanate), 25 mM non-chotropic salt (e.g., sodium citrate), a reducing agent (e.g., beta-mercaptoethanol), and having a neutral pH (e.g., pH 7.5);

To lysate, add binding reagent containing 0-100% sulfolane to achieve a final sulfolane concentration of from 0-70% (e.g., 5%-70%, 10%, 20%, 30%, 40%, 50%) to make a mixture;

Apply mixture to a mineral support by way of gravity, centrifugation, positive pressure and/or vacuum, etc. (e.g., centrifugation in a table-top microcentrifuge at top speed for about 15 seconds);

Separate flow-through (eluate) from mineral support;

Wash mineral support once or twice with wash buffer containing high salt and ethanol (e.g., 1 to 3 M guanidinium thiocyanate, 25 mM Tris pH 7.5, 10-30% ethanol)—the amount of ethanol in the wash buffer can be adjusted up or down to improve purification of RNA vs. DNA. (The higher percentage of ethanol in the wash, the more DNA is eluted.)

Wash mineral support once or twice with wash buffer, such as a low salt wash buffer, comprising 80% ethanol in water;

Optionally wash mineral support in acetone;

Air dry mineral support (e.g., by way of centrifugation, positive pressure and/or vacuum without adding liquid);

Elute bound RNA with water or an aqueous solution (low salt), which can be room temperature or higher (e.g., 80° C.).

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

Sequence Listing beta-globin sense primer:
5'-TGCACGTGGATCCTGAGAACT-3' (SEQ ID NO:1)
beta-globin anti-sense primer:
5'-AATTCTTTGCCAAAGTGATGGG-3' (SEQ ID NO:2)
probe for beta-globin:
5'-FAM/CAGCACGTTGCCCAGGAGCCTG/3BHQ_1/-3' (SEQ ID NO:3)

The invention claimed is:

1. A method for the separation of a nucleic acid from other biological molecules present in a sample, said method comprising:
applying an aqueous sample comprising at least one nucleic acid and at least one other biological molecule to at least one mineral substrate in the presence of one or more salts and sulfolane, wherein the concentration of the sulfolane is 15% to 80% by volume, and wherein the mineral substrate adsorbs at least one nucleic acid to create a mineral substrate-nucleic acid complex and a composition not adsorbed to the mineral substrate; and
removing at least a portion of the composition not adsorbed to the mineral substrate, thereby separating the nucleic acid from at least one other biological molecule present in the sample.

2. The method of claim 1, wherein the sample comprises DNA, RNA, or both.

3. The method of claim 2, wherein the sample further comprises a protein, and the protein is purified as a result of not binding to the mineral substrate.

4. The method of claim 1, wherein the concentration of the sulfolane is about 35% to 50% by volume.

5. The method of claim 1, wherein the mineral substrate-nucleic acid complex comprises DNA and RNA, and wherein the method further comprises digesting the DNA of the complex with DNase.

6. A method for the separation of DNA from RNA in a sample, said method comprising:
applying an aqueous sample comprising DNA and RNA to a first mineral substrate in the presence of one or more salts and in the absence of sulfolane, wherein the first mineral substrate retains predominantly the DNA and wherein the action of applying the aqueous sample results in a filtrate that is essentially devoid of the DNA, and
applying the filtrate to a second mineral substrate in the presence of one or more salts and sulfolane, wherein the concentration of the sulfolane is about 15% to 50% by volume, and wherein the action of applying the filtrate to the second mineral substrate results in binding of predominantly RNA,
thereby separating DNA in the sample from RNA in the sample.

7. The method of claim 6, wherein the concentration of the sulfolane is about 35% to 50% by volume.

8. The method of claim 6, wherein the DNA comprises genomic DNA.

9. The method of claim 8, wherein the genomic DNA is predominantly retained on the first mineral substrate.

10. The method of claim 9, further comprising recovering the genomic DNA from the first mineral substrate by eluting the genomic DNA from the first mineral substrate.

11. The method of claim 6, wherein the first mineral substrate and the second mineral substrate are the same.

12. The method of claim 6, further comprising, after applying the filtrate to the second mineral substrate, treating the second mineral substrate with DNase.

13. The method of claim 6, wherein the one or more salts present in the aqueous sample applied to the first mineral substrate and in the filtrate applied to the second mineral substrate comprise a chaotropic salt or a combination of guanidinium thiocyanate and at least one other chaotropic salt.

14. A method for the separation of RNA from other biological molecules present in a sample, said method comprising:
    applying a sample comprising RNA and at least one other biological molecule to at least one mineral substrate in the presence of one or more salts and sulfolane, wherein the sulfolane concentration is 15% to 80% by volume, and wherein the mineral substrate binds the RNA; and
    removing at least a portion of the sample not adsorbed to the mineral substrate,
    thereby separating the RNA from at least one other biological molecule present in the sample.

15. The method of claim 14, wherein the sulfolane concentration is about 35% to 50% by volume.

16. The method of claim 14, wherein the one or more salts comprises a chaotropic salt or a combination of guanidinium thiocyanate and at least one other chaotropic salt.

17. A composition comprising:
    a mineral substrate; and
    an aqueous composition comprising one or more salts and sulfolane, wherein the sulfolane concentration is 15% to 80% by volume.

18. The composition of claim 17, further comprising a nucleic acid.

19. The composition of claim 17, wherein the sulfolane concentration is about 35% to 50% by volume.

20. A kit comprising:
    at least one mineral substrate; and
    at least one container holding an aqueous composition comprising one or more salts and sulfolane, wherein the sulfolane concentration is 15% to 80% by volume.

21. The kit of claim 20, further comprising at least one container holding at least one nucleic acid.

22. The kit of claim 20, wherein the sulfolane concentration is about 35% to 50% by volume.

* * * * *

UNITED STATES PATENT AND TRADEMARK OFFICE
CERTIFICATE OF CORRECTION

PATENT NO.        : 8,686,129 B2
APPLICATION NO.   : 11/688652
DATED             : April 1, 2014
INVENTOR(S)       : Jeffrey C. Braman et al.

Page 1 of 1

It is certified that error appears in the above-identified patent and that said Letters Patent is hereby corrected as shown below:

On the Title Page, in Item (56), under "Other Publications", in column 2, line 13, delete "frm" and insert -- from --, therefor.

On the Title Page, in Item (57), under "Abstract", in column 2, line 4, delete "sufolane." and insert -- sulfolane. --, therefor.

Signed and Sealed this
Twenty-fourth Day of June, 2014

Michelle K. Lee
*Deputy Director of the United States Patent and Trademark Office*